United States Patent [19]

Kogut et al.

[11] Patent Number: 5,891,443
[45] Date of Patent: *Apr. 6, 1999

[54] METHOD TO PRODUCE GRANULOCYTE COLONY STIMULATING FACTOR FROM IMMORTALIZED AVIAN T LYMPHOCYTES TO PRODUCE IMMORTALIZED CELLS

[75] Inventors: Michael H. Kogut, College Station, Tex.; John R. DeLoach, Lenoir, Tenn.; Larry H. Stanker, College Station, Tex.; Rita B. Moyes, College Station, Tex.; Billy M. Hargis, College Station, Tex.

[73] Assignees: The United States of America as represented by the Secretary of Agriculture, Washington, D.C.; The Texas & M University System College, Station, Tex.

[21] Appl. No.: 929,074

[22] Filed: Sep. 15, 1997

Related U.S. Application Data

[63] Continuation of Ser. No. 675,749, Jul. 3, 1995, Pat. No. 5,691,200.

[51] Int. Cl.$^6$ .................. A61K 39/002; A61K 39/02; A61K 39/12; C12P 21/00
[52] U.S. Cl. ..................... 424/204.1; 424/234.1; 424/258.1; 424/269.1; 435/69.5; 435/70.5; 435/349; 435/390
[58] Field of Search ............... 435/70.5, 172.3, 435/349, 390, 69.5; 424/204.1, 207.1, 234.1, 258.1, 269.1

[56] References Cited

U.S. PATENT DOCUMENTS 5,691,200  11/1997  Kogut et al. ....................... 435/349

OTHER PUBLICATIONS

Tellez, G.I., Kogut, M.H., Hargis, B.M., "Immunoprophylaxis of *Salmonella enteritidis*Infecton by Lymphokines in Leghorn Chicks." *Avian Diseases*, 1993, vol. 37, pp. 1062–1070.

Hoelzer, J.D., Franklin, R.B., Bose Jr., H.R., "Transformation by Reticuloendotheliosis Virus: Developement of a Focus Assay and Isolation of a Nontransforming Virus." *Virology*, 1979, vol. 93, pp. 20–30.

Schat, K.A., Pratt, W.D., Morgan, R., Weinstock, D., Calnek, B.W. "Stable Transfection of Reticuloendotheliosis Virus–Transformed Lymphoblastoid Cell Lines." *Avian Diseases*, 1992, vol. 36, pp. 432–439.

Benatar, T., Iacampo, S., Tkalec, L., Ratcliff, M.J.H. "Expression of Immunoglobulin Genes in the Avian Embryo Bone Marrow Revealed by Retroviral Transformation," *Eur. J. Immuno.*, vol. 27, 1991, pp. 2529–2536.

Benatar, T., Tkalac, L., Ratcliffe, M.J.H. "Stochastic Rearrangement of Immunoglobulin Variable–Region Genes in Chicken B–cell Development," *Proc. Natl. Acad. Sci., USA*, Aug., 1992, vol. 89, pp. 7615–7619.

Weber, F., Meinl, E., Drexler, K., Czlonkowska, A., Huber, S., Fickenscher, H., Muller–Fleckenstein, I., Fleckenstein, B., Wekerle, H., Hohlfeld, R. "Transformation of Human T–Cell Clones by Herpesvirus Saimiri: Intact Antigen Recognition by Autonomously Growing Myelin Basic Protein–Specific T Cells," *Proc. Natl. Acad. Sci. USA*, Dec. 1993, vol. 90, pp. 11049–11053.

Stephens, R.M., Rice, N.R., Hiebsch, R.R., Bose Jr., H.R., Gilden, R.V. "Nucleotide Sequence of v–rel: The Oncogene of Reticuloendotheliosis Virus," *Proc. Natl.* Acad. Sci. USA, Oct., 1983, vol. 80, pp. 6229–6233.

Kogut, M.H., McGruder, E.D., Hargis, B.M., Corrier, D.E., DeLoach, J.R. "In Vivo Activation of Heterophil Function in Chickens Following Injection with *Salmonella Enteritidis*–Immune Lymphokines," *Journal of Leukocyte Biology*, Jan. 1995, vol. 57, pp. 56–62.

McGruder, ED et al. Poultry Science. 72:2264–2271, 1993.
Marmor, MD et al. J. Exp. Med. 177:647–656, Mar. 1993.

*Primary Examiner*—David Saunders
*Assistant Examiner*—F. Pierre VanderVegt
*Attorney, Agent, or Firm*—M. Howard Silverstein; Randall E. Deck; John D. Fado

[57] ABSTRACT

Immortal avian T lymphocyte cell lines which produce and secrete immune lymphokines are disclosed. These cell lines may be produced from T cells recovered from fowl which have been hyperimmunized in vivo. The activated T cells are first exposed in vitro to a mitogen effective for secondary stimulation thereof, and then virally transformed to produce an immortal cell line. When cultured in vitro, the cell lines produce and secrete immune lymphokines which may be administered to fowl to increase their resistance to infections.

13 Claims, 4 Drawing Sheets

METHOD TO PRODUCE GRANULOCYTE COLONY STIMULATING FACTOR FROM IMMORTALIZED AVIAN T LYMPHOCYTES TO PRODUCE IMMORTALIZED CELLS

This application is a continuation of application Ser. No. 08/675,749 filed Jul. 3, 1995, now U.S. Pat. No. 5,691,200, the contents of which are incorporated by reference herein.

BACKGROUND OF THE INVENTION

1. Field of the Invention

This invention relates to the production of immortalized cell lines from avian T lymphocytes, and the use of those cell lines to produce immune lymphokines.

2. Description of the Prior Art

Earlier studies have shown that Salmonella enteritidis (SE)-immune chicken T cell lymphokines from non-transformed cells (SEILK) are efficacious against experimental SE infections in 1-day-old and 18-day-old leghorn chicks (McGruder et al., 1993, Poultry Sci., 72:2264–2271, and Tellez et al., 1993, Avian Dis., 37:1062–1070). When these lymphokines (SEILK) were administered intra peritoneally (i.p.) to chicks thirty minutes before SE challenge, protection against SE organ invasion occurred within 24 hr. However, when lymphokines from normal, non-immune avian T cells were administered prophylactically, protection against SE organ invasion was not observed (McGruder et al., 1993, and Tellez et al., 1993, ibid). The increased resistance to infection seen with SEILK administration is characterized by a heterophilic inflammatory influx into the peritoneal cavity which peaks at 4 hr after challenge injection. Heterophils isolated from SEILK injected chicks displayed increased inflammatory reactivity when tested in vitro for adherence, chemotaxis, phagocytosis of SE, and killing of SE, *S. typhimurium, S. gallinarum,* and *Escherichia coli* as compared to heterophils from saline injected control birds (Kogut et al., 1995, J. Leuk. Biol., 57:56–62). Hypothetically, SEILK injection induces a heterophilia and activation of these cells while the invasive process of the SE provides the secondary signal for the site of the inflammatory response resulting in increased phagocytosis and killing of the invading organism. Consequently, there is a greatly reduced bacterial invasion into the parynchymal organs.

To date, all studies utilizing SEILK have involved the tedious task of repeatedly making batches of SEILK from hyperimmunized chickens for continued experimental use. Viral transformation has been demonstrated with human T cell clones using *Herpesvirus saimiri* (Weber et al., 1993, Proc. Natl. Acad. Sci. USA, 90:11049–11053), producing immortal cells which are easy to grow in culture. Recently, retroviral transformation in vitro of chicken T cells has been demonstrated using the reticuloendotheliosis virus strain T (REV-T). REV-T, a replication defective avian retrovirus, transforms avian hematopoietic cells due to the integration of the oncogene, v-rel, into the host cell genome (Hoelzer et al., 1979, Virology, 93:20–30, and Stephens et al,. 1983, Proc. Natl. Acad. Sci. USA, 80:6229–6233). When the helper virus chicken syncytial virus (CSV) is introduced, virus particles are produced that are tropic but not cytopathic for transformed lymphocytes (Barth and Humphries, 1988, J. Exp. Med., 167:89–108). B cells are transformed exclusively when ex vivo spleen cells are exposed to REV-T (CSV) transformation, while pre-mitogen stimulation of spleen cells yield predominantly transformed T cells (Marmor et al., 1993, J. Exp. Med., 177:647–656; and Schat et al., 1992, Avian Diseases, 36:432–439). However, the transformation of the T cells was only short term. Apparently, the transformed T-cells were not truly immortal, but required the addition of exogenous interleukins to maintain growth (Marmor et al., ibid).

SUMMARY OF THE INVENTION

We have now discovered immortal avian T lymphocyte cell lines which produce and secrete immune lymphokines. These cell lines may be produced from T cells recovered from fowl which have been hyperimmunized in vivo. The activated T cells are first exposed in vitro to a mitogen effective for secondary stimulation thereof, and then virally transformed to produce an immortal cell line- When cultured in vitro, the cell lines produce and secrete immune lymphokines which may be administered to fowl to increase their resistance to infections.

It is an object of this invention to provide a method to immortalize avian T lymphocytes from hyperimmunized fowl.

Another object of this invention is to provide immortal avian T lymphocyte cell lines that produce and secrete immune lymphokines in vitro.

A further object of this invention is to provide immortal avian T lymphocyte cell lines which produce and secrete immune lymphokines that prevent or reduce infection by pathogenic microorganisms.

Other objects and advantages of this invention will become readily apparent from the ensuing description.

DETAILED DESCRIPTION OF THE INVENTION

Figure 1:
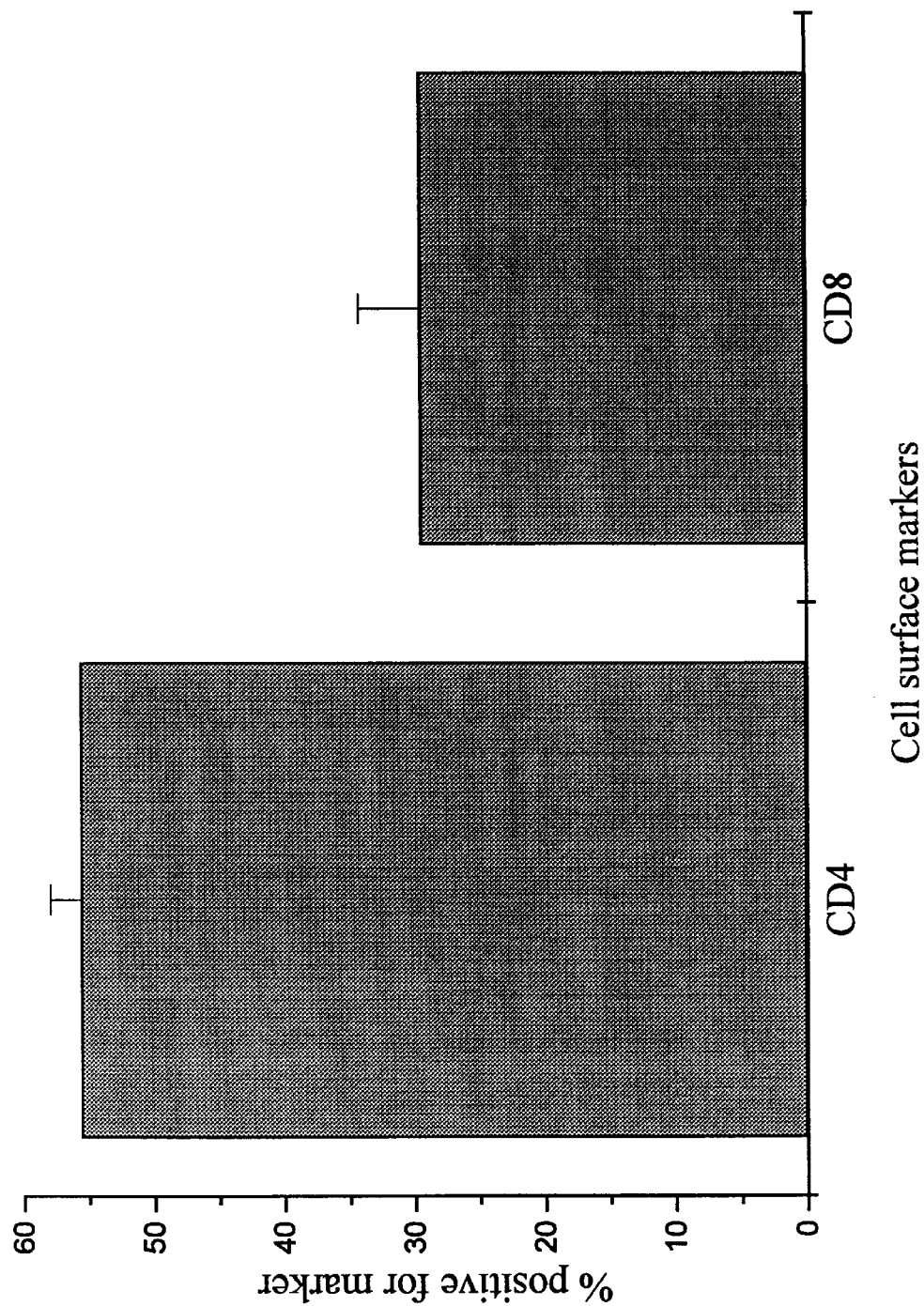
FIG. 1. Fourteen to eighteen days after initial virus transformation, transformed virus spleen cells were labeled with anti-chicken CD4 or anti-chicken CD8 monoclonal antibodies followed by FITC-conjugated anti-mouse-IgG. Each bar represents the mean±sem of percent positive cells to the cell surface marker indicated of 8 lines tested in triplicate.

The cell lines of this invention are derived from mature T lymphocytes (T cells) which have been recovered or isolated from fowl. The invention may be practiced with T cells from any type of fowl, although poultry, including turkeys, ducks, quail, geese, pheasant, and particularly chickens, are preferred sources. However, the fowl selected as the source for the T cells should be immunologically competent or mature adults, having immune systems wherein the T cells may be effectively activated or stimulated in response to inoculation with an antigen of interest.

The process of the invention may be used to produce cell lines secreting immune lymphokines which are protective against infection of fowl by a wide variety of target microorganisms. Without being limited thereto, the process is useful for providing protection against viral, bacterial, fungal, and protozoan avian pathogens, particularly against pathogens of poultry such as described in Calnek et al. (1991, Diseases of Poultry, ninth ed., Iowa State University Press, Ames, Iowa), the contents of which are incorporated by reference herein. The immune lymphokines so produced are effective for reducing the incidence or severity of infection of fowl by a target pathogen. The invention may be practiced with any of the above mentioned fowl, particularly poultry, and most particularly chickens.

To produce the immune lymphokines, the fowl are first immunized with an immunogen in vivo. The immunogen should be administered to the fowl in an amount effective to activate or stimulate the T cells of that animal, that is, to induce cellular immunity mediated by T cells. The actual amount may be readily determined, and will vary with the immunogen, its formulation, the route and schedule of administration, and the subject animal. In a preferred embodiment, the immunogen is administered to the fowl repeatedly (i.e. hyperimmunization), with at least one and most preferably two or three booster doses being administered after the initial inoculation, to produce T cells at a high activation state and effect maximal build-up of memory T cells specific for the target immunogen. While the immunization schedule is not critical, the doses are generally administered at approximately one week intervals. Inoculation of the animals may be made by various routes, although oral administration or injection are preferred. Optionally, the immunogen may be formulated with a pharmaceutically acceptable carrier to facilitate administration. The skilled practitioner will recognize that other routes of administration, immunization schedules, carriers or conventional adjuvants may be used.

The immunogens used to activate the T cells include but are not limited to immunogens of microorganisms pathogenic to fowl, particularly viruses, bacteria, fungi, and protozoa. Preferred for use herein are immunogens of pathogens of poultry, particularly Salmonella spp., such as S. enteriditis, pathogenic *Escherichia coli*, and Eimeria spp., such as E. tenella.

The immunogen may consist of, or be derived from, the target microorganism. In accordance with a preferred embodiment, the viable microorganism is used as the immunogen. However, the skilled practitioner will recognize that attenuated, killed, or inactivated microorganisms may be used as immunogens, as well as mutants or components or fragments thereof, as are conventional in the art. Suitable immunogens for use herein may be readily determined and include, for example, those described by Calnek et al. (ibid) for immunization of poultry against a variety of pathogens.

Activated T lymphocytes may be recovered from the fowl after the immunization. Generally, the cells may be harvested about one to three weeks, preferably two weeks, after the last immunization, to achieve a maximum activation state. However, the actual timing of the harvest will vary with the specific immunogen, the immunization dosage, and schedule. For use herein, mature T cells can be harvested from any source, including peripheral or lymphoid T cells or mixtures thereof, although splenic T cells are preferred.

The recovered T cells may be used in pure or impure form. Although neither B-cells nor macrophages interfere with the process of this invention and appear to eventually die off, these and other cell types may nonetheless be removed to ensure purity of the T cells. Separation of the lymphocytes in general, or separation of the T cells in particular, from other cells may be performed using well known techniques, such as by density gradient centrifugation or absorption. In the preferred embodiment, splenic lymphocytes may be separated by contacting suspended cells with a plastic surface to remove adhering macrophages. T cells may be further separated from B-cells, for example, by affinity chromatography. In one embodiment, B-cells may be removed by absorption, for example, with nylon wool. The T cells may be readily eluted from the substrate while B-cells remain adhered.

Following their recovery from the immunized animal, the activated T cells are first exposed in a culture media in vitro, to a mitogen in an amount effective to further stimulate or activate the cells to division or blastogenesis. Techniques for in vitro lymphocyte activation which may be used herein are well known in the art, as are a variety of mitogens, and include those described by Weiler and Von Bulow (1987, Vet. Immunol. Immunopathol., 14:257–267) and Stites [Clinical Laboratory Methods for Detection of Cellular Immune Function, In: *Basic & Clinical Immunology*, fifth edition, Stites et al. (ed.), Lange Medical, Los Altos, Calif., (1984), pp. 362–365], the contents of each of which are incorporated by reference herein. Weiler and Von Bulow (ibid) also described the optimal conditions, including mitogen concentration, culture media, and environmental conditions for lymphokine production. Without being limited thereto, preferred mitogens for use herein include phytohemagglutinin (PHA), phorbol myristate acetate (PMA), and particularly concanavalin A (Con A). In brief, the T cells are suspended in a suitable tissue culture medium with added mitogen and incubated, preferably at about 37° C. in a $CO_2$ containing atmosphere, for approximately 48 to 72 hours. The amount of mitogen added to the media may be readily determined, and will vary with the particular mitogen selected and the cell concentration.

Once the T cells have been activated with mitogen, they may be virally transformed using a reticuloendotheliosis virus (REV). Transformation may be effected using any strain of REV, although REV strain T (REV-T), a replication defective strain described by Thielen et al. (1966, J. Natl. Cancer Inst., 37:731) and Chen et al. (1981, J. Virol., 40:800), is preferred. When using REV-T, it is necessary to include a helper virus such as chicken syncitial virus (CSV), as described by Barth and Humphries (ibid) and Benatar et al. (1991, Eur. J. Immunol., 21:2529; and 1992, Proc. Natl. Acad. Sci. USA, 89:7615). The mitogen activated T cells are suspended in a suitable tissue culture medium to which REV is added in an amount effective to transform the cells, and incubated.

The culture media and conditions per se which are used in the transformation are not critical, and may be the same as used for the in vitro activation. A variety of conventional culture media, which may contain serum or be serum-free, and culture conditions are suitable for use herein. Without being limited thereto, transformation is preferably conducted in RPMI containing fetal calf serum or calf serum incubated at about 37° C.

In a particularly preferred embodiment, transformation is carried out in the presence of added mitogen. Without wishing to be bound by theory, it is believed that addition of mitogen to the culture media during transformation allows continued expression or activation of receptors, which were previously present as a result of the in vivo immunization. Furthermore, addition of mitogen to the culture media is essential to effect optimum production of the immune lymphokines. In the absence of mitogen, production and secretion of immune lymphokines by the T cells (both activated and transformed) will be severely diminished.

Transformation of the REV treated T cells is indicated by cell growth in comparison to control cells not REV. T cells which have been transformed and grown in mitogen containing culture media may then be screened to select for those transformants producing and secreting immune lymphokines. Screening is generally carried out in vivo by selecting those cell lines which demonstrate efficacy for inhibiting infection of fowl by the target microorganism. Samples of the cells or the supernatant culture fluid are administered to pathogen-free animals, and the animals are challenged with a viable sample of the target microorganism. After incubation, the animals are examined for evidence of infection or pathogenicity. Effective protection against the microorganism and production of immune lymphokines are indicated by a reduced incidence of infection or pathogenicity in the treated population relative to an untreated control.

After the T cells have been transformed, they may be recovered for use as described. The transformed T cell lines may be expanded or subcultured onto fresh culture media without REV, or stored in liquid nitrogen for later use. Surprisingly, we have found that the transformed T cell lines remain stable (immortal) throughout prolonged cultivation on conventional culture media. Furthermore, unlike the T cell lines described by Marmor et al. (1993, J. Exp. Med., 177:647–656) or Schat et al. (1992, Avian Diseases, 36:432–439), the transformed T cell lines of this invention remain stable even without the addition of exogenous interleukins (IL-2) to the culture medium.

Large quantities of the immune lymphokines may be produced by culture of the transformed cell lines as described above. The lymphokines produced by the cell lines will be secreted into the culture medium and may be recovered therefrom. As before, to effect optimum production of the immune lymphokines by the transformed cells, mitogen must be added to the culture medium. Although the transformed cells will remain stable and continue to grow indefinitely in the absence of mitogen, they will produce only minimal amounts of immune lymphokines. Interestingly, transformed cells may be cultured in mitogen-free media until such time as production of immune lymphokines is desired. Production and secretion of the immune lymphokines may then be stimulated by addition of mitogen to the culture media and will continue indefinitely until the mitogen has been consumed by the replicating cells. The mitogen concentration and culture conditions may be the same as those described for the in vitro activation.

Following production, the immune lymphokines may be administered directly to the subject fowl. Because the immune lymphokines are secreted, either a crude preparation of a culture of the transformed cells, or the culture supernatant free of cells, may be recovered for use. Use of crude extracts or supernatants obviates the need for purification and is preferred. It is also understood that the immune lymphokines may also be purified, such as by conventional chromatography or gel electrophoresis techniques. Optionally, the preparation containing the immune lymphokines may be further formulated with a conventional inert carrier to facilitate administration. Adjuvants conventional in the art for the treatment of fowl, including those for the treatment of enteropathogens, may also be formulated with the immune lymphokines. Suitable adjuvants include, for example, antibiotics, coccidiostats or lactose.

Administration of the immune lymphokines may be at any time during the life of the animal. However, in the preferred embodiment, the lymphokines are administered to newly hatched fowl between about one to fourteen days old. The preparations of the immune lymphokines may be administered by any convenient route, such as by intraperitoneal (i.p.), subcutaneous, or intramuscular injection. The preparations are generally administered by i.p. injection, such as described by McGruder et al. (McGruder et al., 1993, Poultry Sci., 72:2264–2271, and Tellez et al., 1993, Avian Dis., 37:1062–1070), the contents of each of which are incorporated by reference herein. In an alternative embodiment, the immune lymphokines may be administered in ovo, such as described by Kogut et al. (U.S. Pat. No. 5,698,193, the contents of which are also incorporated by reference herein.

The immune lymphokines are administered in an amount effective to substantially reduce the incidence of infection (as determined by the number of animals infected or the severity or pathogenicity of infection) resulting from a target microorganism in a treated bird, in comparison with untreated controls. Suitable amounts may be readily determined by the practitioner skilled in the art, and will vary with the age and size of the bird, and the target pathogen.

The immune lymphokines produced by the transformed cell lines of this invention function in the same manner as granulocyte-colony stimulating factor (G-CSF). When administered to fowl, the lymphokines induce a granulocytic (PMN) inflammatory response when the fowl are challenged with the target pathogen. This inflammatory response is characterized by: (a) a dramatic emigration of granulocytic cells from the bone marrow into the peripheral blood, (b) an enhancement of the biological functions (activation) of the circulating PMNs, and (c) a directed influx of these activated PMNs to the site of invasion by the pathogen.

As shown in Example 1 below, during approximately the first two months following transformation, the cell lines retain the characteristic T cell surface markers, including CD4 and CD8, which were present in vivo in the parent T cells from which they were derived. Thus, if a mixture of different T cells is harvested and treated as described, the various T cell types are briefly conserved after completion of the transformation. However, after prolonged cultivation, generally after about two months, the T cell markers gradually disappear until the remaining cells appear indistinguishable. This loss of surface markers has no effect on the cells lines, capability to produce and secrete immune lymphokines.

Although it is preferred to prepare the cell lines of this invention from mixtures of T cells as described, such as from a spleen, it is envisioned that the cell liner could be produced from specific T cell populations. Those resultant transformed cell lines producing immune lymphokines may be identified when screened. Moreover, although the transformed cells have not been cloned, it is envisioned that the cells could be cloned using conventional techniques. The ability of any resultant clones to produce immune lymphokines may be confirmed by screening.

The following examples are intended only to further illustrate the invention and are not intended to limit the scope of the invention which is defined by the claims.

EXAMPLE 1

Materials and Methods

Experimental Animals

One-day-old Leghorn chicks (HyLine W-36) were obtained from a commercial hatchery and were randomly distributed in a commercial electrically heated brooder battery (Petersime Incubator Co., Gettysburg, Oh., 45328) set up within a biological hazard isolation unit located on the research farm of the College of Veterinary Medicine, Texas A&M University, in accordance with approved USDA guidelines. Chicks were provided ad libitum access to water and a balanced unmedicated corn-soybean ration. The feed ration contained or exceeded the levels of critical nutrients recommended by the National Research Council (1984). Salmonella were not detected in either the feed rations or the paper liners of the chick transport containers as determined by previously described procedures (Andrews et al., 1978, Isolation and Identification of Salmonella, In: Bacteriological Analytical Manual, fifth edit., Assoc. Official Anal. Chem., Washington, D.C.). *Salmonella enteritidis*

A primary poultry isolate of SE from the National Veterinary Services Laboratory, Ames, IA, and approved by the USDA Animal and Plant Health Inspection Service for use in the authors' laboratory, was selected for resistance to novobiocin-nalidixic acid and maintained on nutrient agar. Medium used to culture the resistant isolate in experimental studies contained 25 µg/ml novobiocin and 20 µg/ml nalidixic acid to inhibit the growth of other bacteria. *Salmonella enteritidis* (SE) challenge inocula were prepared in sterile phosphate buffered saline (PBS). The viable cell concentration of the inoculum was verified by colony counts on brilliant green agar (BGA; Difco Laboratories, Detroit, MI 48232) plates.

SE-Immune Lymphokine (SEILK) Production (by non-transformed cells)

Fifty 42-week-old layer hens (Hy-Line W-36), determined to be sero-negative and feces culture negative for Salmonella, were immunized by oral gavage with $10^6$ cfu of SE. On days 7, 14, and 21 postimmunization, the hens were boosted via gavage with the same dose of SE. SEILK production was adapted from the procedure of Kogut and Slajchert (1992, Immunol. Infect. Dis., 2:69–80), the contents of which are incorporated by reference herein. Briefly, two weeks after the last challenge, the spleens were aseptically harvested and pooled. A single cell suspension was prepared in serum-free RPMI supplemented with L-glutamine, sodium pyruvate, and antibiotic/antimycotic solution (Sigma, St. Louis, Mo. 63178). The spleen cell suspension was enriched for T cells according to the procedures of Kogut and Slajchert (ibid). This spleen cell suspension was incubated in 150×25 mm plastic Petri dishes for 4 hr at 37° C. in a 5% $CO_2$ incubator to remove the adherent cells (macrophages). The nonadherent cells (lymphocytes) were washed from the petri dishes and applied to sterile nylon wool (Polysciences, Warrington, Pa. 18976) columns and incubated for 1 hr at 37° C. in a 5% $CO_2$ incubator. The cells that did not adhere to the nylon wool (T lymphocytes) were eluted from the column with warm RPMI. The eluted cells were checked for viability based on 0.1% trypan blue dye exclusion (Freshney 1983, Culture of Animal Cells, Vol. 1, Alan R. Liss, New York), and the cell density was adjusted to $1\times10^9$ cells/ml. The enriched T cell suspension was then added to 175 cm² tissue culture flasks at 1 ml/100 ml of media containing 7.5 ug Con A/ml and incubated for 48 hr at 37° C. in a 5% $CO_2$ incubator. After incubation, the supernatant fluids were collected and centrifuged at 2000×g for 15 min to remove all cells. The supernatant was concentrated fivefold by ultrafiltration using YM-10 membranes (Amicon Corp., Beverly, Mass. 01915). The resulting retentate was filtered through a 0.45 µm filter and stored in aliquots at −20° C. until used.

Virus Transformation

Avian reticuloendotheliosis virus (REV-T with CSV) was purchased from the ATCC (VR-770, Rockville, MD 20852). Whole spleen cell suspensions from SE hyperimmunized birds were seeded in 24 well plates at $20\times10^6$ cells/2ml/well plus 7.5 ug/ml of Concanavalin A (Con A) (Sigma) and incubated for 72 hr at 37° C. in a 5% $CO_2$ incubator. One vial containing 1 ml of virus ($10^7$TCID/ml) was mixed at 0.5 ml of virus plus 24 ml of RPMI+FCS/CS containing 7.5 µg of ConA/ml. At this point, the cells were virally transformed by the addition of 1 ml/well of the virus containing media. Transformation of cells was assessed by microscopic examination of cell growth as compared to non-transformed controls. Within 15 days, growth of the transformed cells had been expanded into 75 cm² flasks. Transformed cells were frozen periodically in 50% FCS, 40% CS, and 10% DMSO and stored in liquid nitrogen for long-term storage. Transformed cell lines were maintained in culture in 75 cm² flasks for lymphokine production as described below. Production of virus was monitored by Scanning Electron Microscopy (SEM) as described below. Viral particles in the supernatant were assayed for by injecting one ml of supernatant of the transformed cell line culture containing SE-immune lymphokine (VILK) i.p. into 20 one-day-old chicks, and starting on day 5 through day 14, the chicks were observed for parenchymal tumorigenesis according to ATCC instructions.

Lymphokine Production by Virally Transformed Cells

Transformed cell lines were maintained in culture in 75 cm² tissue culture flasks using RPMI+5% FCS. For lymphokine production, cells were taken from maintenance cultures and washed in RPMI and transferred to a 175 cm² flask at $1-5\times10^6$ cells/ml in serum free RPMI containing 7.5 µg Con A/ml and incubated for 72 hr at 37° C. in a 5% $CO_2$ incubator. After incubation, the supernatant fluids were collected, filtered, and stored as above. Transformed T cell line suspensions were assessed by microscopic examination of Hema 3 stained (Curtin Matheson Scientific, Houston, Tx. 77038) cytospin (Shandon Scientific, Pittsburgh, Pa. 15275) smears.

Transmission Electron Microscopy

Cells in suspension were resuspended in 5 ml PBS to which 5 ml of 3% glutaraldehyde in 50 mM phosphate, 50 mM sucrose buffer (pH 7.4) plus 12% picric acid was added. After a 60 min fixation at 24° C., cells were stored at refrigerator temperature until ready for further processing. The cells were then rinsed once in 100 mM phosphate buffer and postfixed in 1% osmium tetroxide prepared in 100 mM phosphate buffer (pH 7.4) containing 100 mM sucrose and 50 mM $KFe(CN)_6$ for 75 min at 4° C. After osmication, samples were rinsed twice in buffer, followed by six rinses in cold distilled water over the course of 1 hr. Samples were then poststained in 1% uranyl acetate for 60 min at 4° C. After 2 rinses in distilled water, samples were embedded in 2% agar, then dehydrated through an ethanol series, followed by acetone, and embedded in Luft's epoxy mixture (Luft, 1961, J. Biophys. Biochem. Cytol., 9:409–414), overnight at 4° C. The resin mixture was exchanged for a solution of 75% epoxy/25% acetone. Samples remained in this mixture for 2 hr at 24° C. Samples were then placed in 100% resin for an additional 2 hr. Embedded samples were then sectioned (0.6–0.8 µm) and observed by TEM (Hitachi H7000, Hitachi Instruments, Mountain View, Calif. 94043).

FACS Analysis

One hundred microliters of RPMI+1% BSA containing $1\times10^6$ cells was added to each eppendorf tube and the primary antibody (anti-CD4 or anti-CD8 monoclonal antibody, Chemicon, Temecula, Calif. 92590) was added as indicated by the manufacturer. The second incubation was with anti-mouse IgG-FITC labeled antibody (Sigma). All incubations took place at 40° C. for 1 hr with gentle agitation and each incubation was followed by 3 washes in RPMI+1% BSA. After staining, all cells were fixed in 500 µl of a 1.5% paraformaldehyde solution in PBS. Cells were also labeled with the second antibody alone to serve as non-specific antibody binding controls. Fluorescence intensity of $10^4$ cells per sample was analyzed by quantitative flow cytometry using a FACSCAN (Becton Dickinson, San Jose, Calif. 95131).

Organ Invasion by *Salmonella enteritidis*

On the day of hatch, chicks were randomly divided into three treatment groups. Birds in one group were each injected i.p. with 0.5ml PBS; birds in the other groups received the same dose of SEILK or VILK. Thirty min after the i.p. injection, all birds were challenged per os with $5\times10^4$ CFU SE. Twenty four hr after SE challenge, the birds in each group were euthanized, and the livers were collected aseptically and cultured for 18 hr at 37° C. in tetrathionate broth. After incubation, the broth was streaked on BGA plates containing NO and NA, incubated for an additional 24 hr at 37° C., and examined for the presence of NO-NA resistant colonies of SE (Andrews et al., ibid). For all studies comparing the effects of SEILK and VILK, the lymphokine preparations were standardized from 100 to 300 ug/ml-based on total protein concentration.

Enumeration of Peritoneal Lavage Heterophils

On the day of hatch, chicks were randomly divided into various treatment groups with 5 birds per group. The chicks were then injected with 0.5 ml of PBS, SEILK, or VILK followed immediately by an i.p. injection of $5\times10^4$ SE. Birds with only PBS and SE-ILK i-p. injections were also included as controls. At 4 hr after injection, chicks were killed by $C_{O2}$ asphyxiation, and their peritoneal cavities lavaged three times with 2 ml of $Ca^{2+}$ and $Mg^{2+}$ free Hank's balanced salt solution containing 0.1 M disodium EDTA and 0.25% BSA (HBSS-EDTA). The peritoneal exudates from individual chicks were placed into centrifuge tubes and maintained in an ice bath. The recovered total leukocyte numbers were counted with a hemacytometer. Separate samples (300 µl) were removed from each peritoneal cell suspension, and cytospin smears were prepared. Smears were air-dried, -then fixed and stained with the Hema 3 staining system (Curtin Matheson Scientific Co., Houston, Tx. 77038). At least 200 leukocytes on each slide were examined microscopically (1000× magnification) and the proportions of mactrophages, polymorphonuclear cells (PMN), and lymphocytes were scored. Because of the low numbers of eosinophils and basophils in chicks, all PMN cells counted were considered to be heterophils (Lucas and Jamroz, 1961, Atlas of Avian Hematology, USDA, Washington, D.C., pp. 155–156). The number of inflammatory heterophils recovered from each chick was used to calculate the mean±SEM inflammatory heterophils per chick (% PMN/chick×total wbc ct/chick= mean heterophil ct/chick).

Peripheral Blood Counts

On the day of hatch, chicks were randomly distributed into 4 groups with 5 chicks each. Birds were treated i.p. with 0.5 ml of (A) PBS with no SE challenge, (B) PBS+SE challenge, (C) SEILK+SE challenge, or (D) VILK+SE challenge. Thirty minutes after treatment, birds in groups B, C, and D were orally challenged with $5\times10^4$ cfu of SE. At 4 hr postchallenge, the chicks were killed by decapitation and 0.1 ml of blood was collected and added to 1.9 ml of diluent (Natt and Herrick, 1952, Poult. Sci., 31:735–738). Total and differential counts were conducted for five birds per treatment group and all counts were performed by an individual without knowledge of the various groups. The total number of leukocytes was then counted in a hemacytometer. Simultaneously prepared blood smears were air-dried, fixed in methanol, and stained and counted as indicated above. The absolute number of heterophils per cubic millimeter were calculated for each chick from the total and differential leukocyte counts. The experiment was conducted 3 times over a one-month period and data from these replicate experiments were pooled for presentation and statistical analysis.

Statistical Analysis

Data from replicate experiments were pooled for the present studies. Differences between treatment groups were determined by one-way analysis of variance and the student's t test using the MicroCal Origin Software Package (Northampton, Mass. 01060).

Results

Transformation

Within 2–3 days of cell culture, transformation was apparent as compared to duplicate plates without virus and the cells had expanded enough by 10 days to freeze down. Microscopic observation of expanded cell lines in tissue culture flasks revealed large non-adherent cell clusters as the characteristic growth pattern. A fibroblastic-like adherent cell line was also observed in the flasks for the first two months but was eventually lost upon continued cell culture. Eight transformed cell lines were tested by FACSCAN analysis for surface markers (FIG. 1) and the cell lines were CD4+(55.6±2.3), CD8+(29.5±4.7), and Ig- so the transformed cell lines were composed of T lymphocytes. Observations of cytospin smears by light microscopy confirmed that the transformed lines were composed mainly of lymphocytes.

Two of the above-mentioned transformed cell lines, designated ConA-C1 and ConA-B1, were retained. Both cell lines were found to produce and secrete immune lymphokines. Cell lines ConA-C1 and ConA-B1 have been deposited under the Budapest Treaty in the American Type Culture Collection (10801 University Boulevard, Manassas, Va. 20110 2209 USA) on Jun. 14 1996, and May 23, 1997, respectively and have been assigned accession numbers ATCC CRL-12135 and ATCC CRL-12357, respectively.

The efficacy results presented below in this Example are for cell line ConA-C1. Analysis of cell line ConA-B1 is described in Example 2.

Transmission Electron Microscopy

The presence of viral particles attached to or budding through the cell membrane of the REV-T transformed chicken spleen cells are evident upon TEM examination and confirms that the "knob" appendages seen on light microscopy is viral budding.

Organ Invasion

Figure 2:
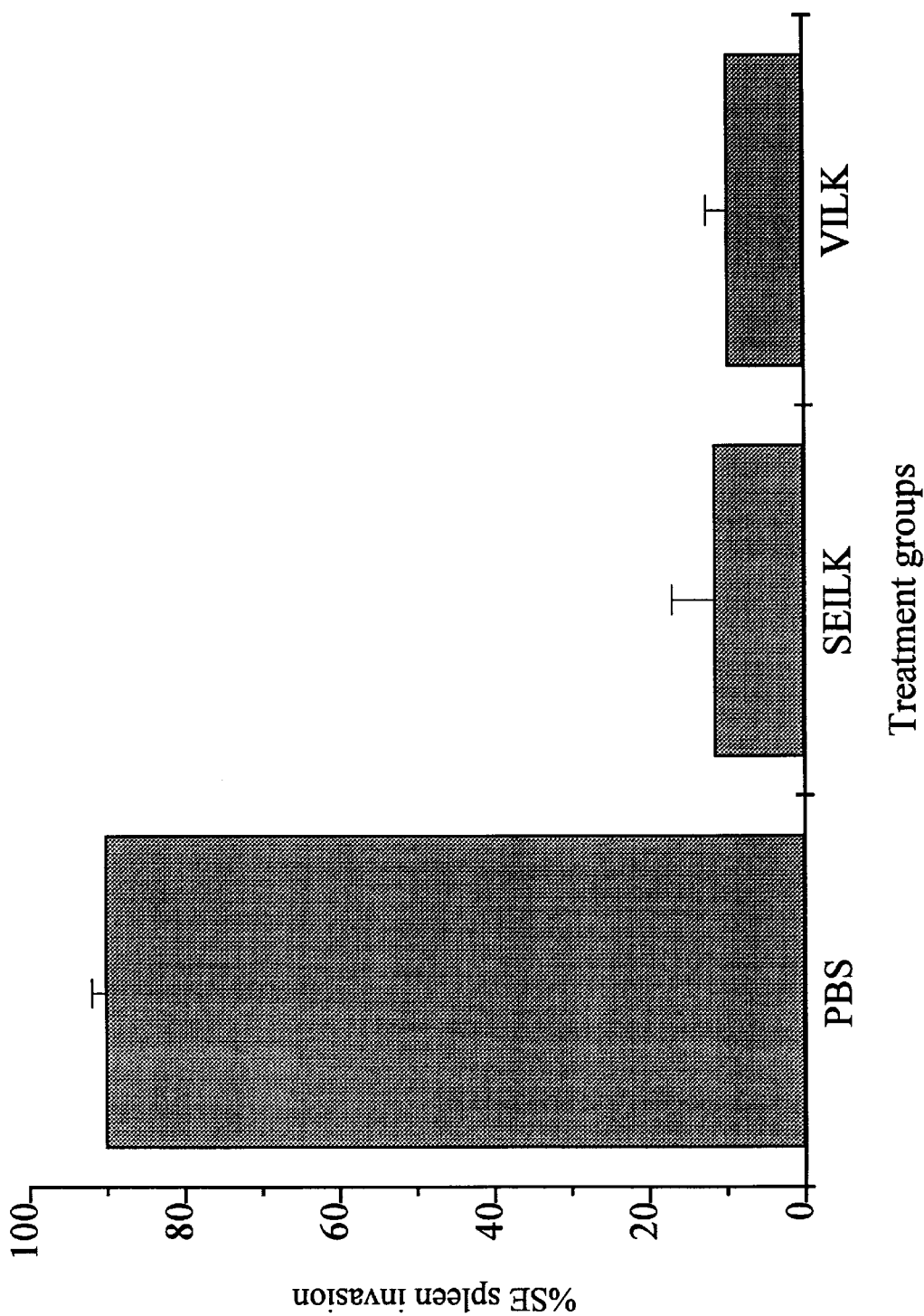
FIG. 2. Comparison of the effects of prophylactic administration of SE-immune chicken T cell lymphokines from non-transformed cells (SEILK) versus SE-immune chicken T cell lymphokines from transformed T cells (VILK) on percent SE spleen invasion in day-of-hatch chicks which were challenged with SE 30 minutes post-injection of lymphokine treatment or PBS control. Each bar represents the mean+sem of percent spleen invasion of 4 experiments consisting of 20 chicks/group per experiment.

Compared to SE positive controls, day old chicks which received prophylactic SEILK or VILK lymphokine treatment 30 minutes prior to SE challenge exhibited a marked reduction in SE spleen invasion (FIG. 2). Spleen invasion was recorded as the percent SE culture positive and the positive control group was 90% positive for spleen invasion compared to 11.5% (SEILK) and 9.8% (VILK) for the pretreatment groups. Both SEILK and VILK reduced organ invasion by approximately 90%.

Inflammatory Cell Recruitment Into the Peritoneum

Figure 3:
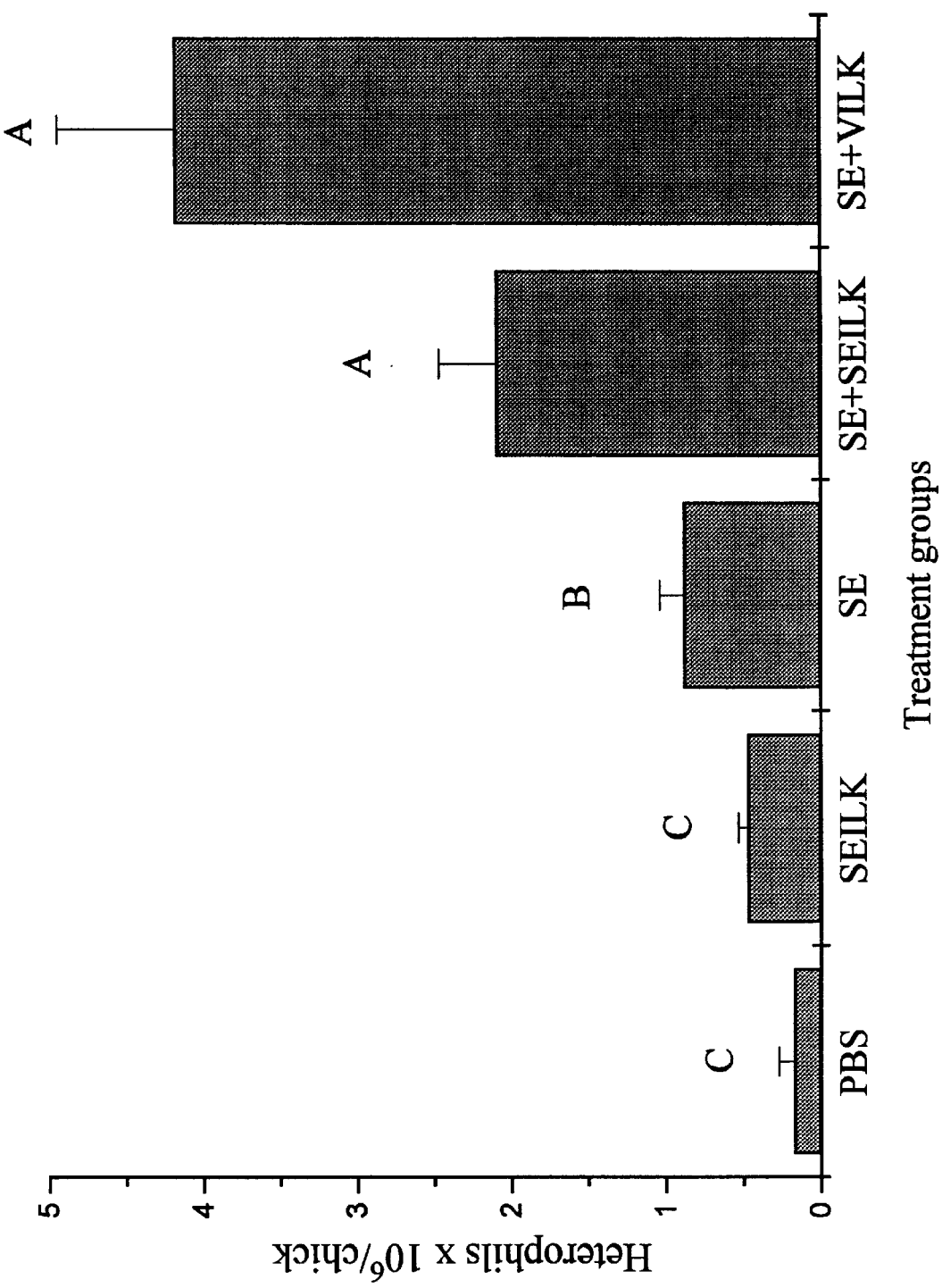
FIG. 3. Recovery of peritoneal heterophils 4 hr after the i.p. injection of either PBS (control), SE-immune lymphokine (SEILK), $5 \times 10^4$ cfu live Salmonella enteritidis (SE), $5 \times 10^4$ cfu live SE and SEILK, or $5 \times 10^4$ cfu live SE and VILK. Each bar represents the mean±sem heterophils×$10^6$ per chick (five chicks/group in each of 5 experiments). Bars with different letters are significantly different ($p<0.01$–$0.001$).

Experiments were conducted to determine if VILK+SE had the capability of inducing an inflammatory response consisting mainly of heterophils as is seen with SEILK+SE injection. It has been previously shown that peak heterophil accumulation occurs at 4 hr after injection (Kogut et al., 1995, Poultry Sci., 74:8–17) so this is the time point used in this experiment. Both SEILK alone and SE only induced a significant heterophilia (p<0.05 and p<0.005, respectively) in the peritoneum as compared to lavage washes from PBS controls (FIG. 3). However, when chicks were injected with SE in combination with SEILK or VILK, there was a significant increase of heterophil numbers (p<0.05 and p<0.01, respectively) as compared to those chicks injected with SE alone. There was no significant difference between the effectiveness of SEILK+SE ($2.09 \times 10^6$ heterophils/chick) and VILK+SE ($4.18 \times 10^6$ heterophils/chick) in inducing a peritoneal heterophilic influx.

Heterophil Peripheral Blood Counts After Lymphokine Administration

Figure 4:
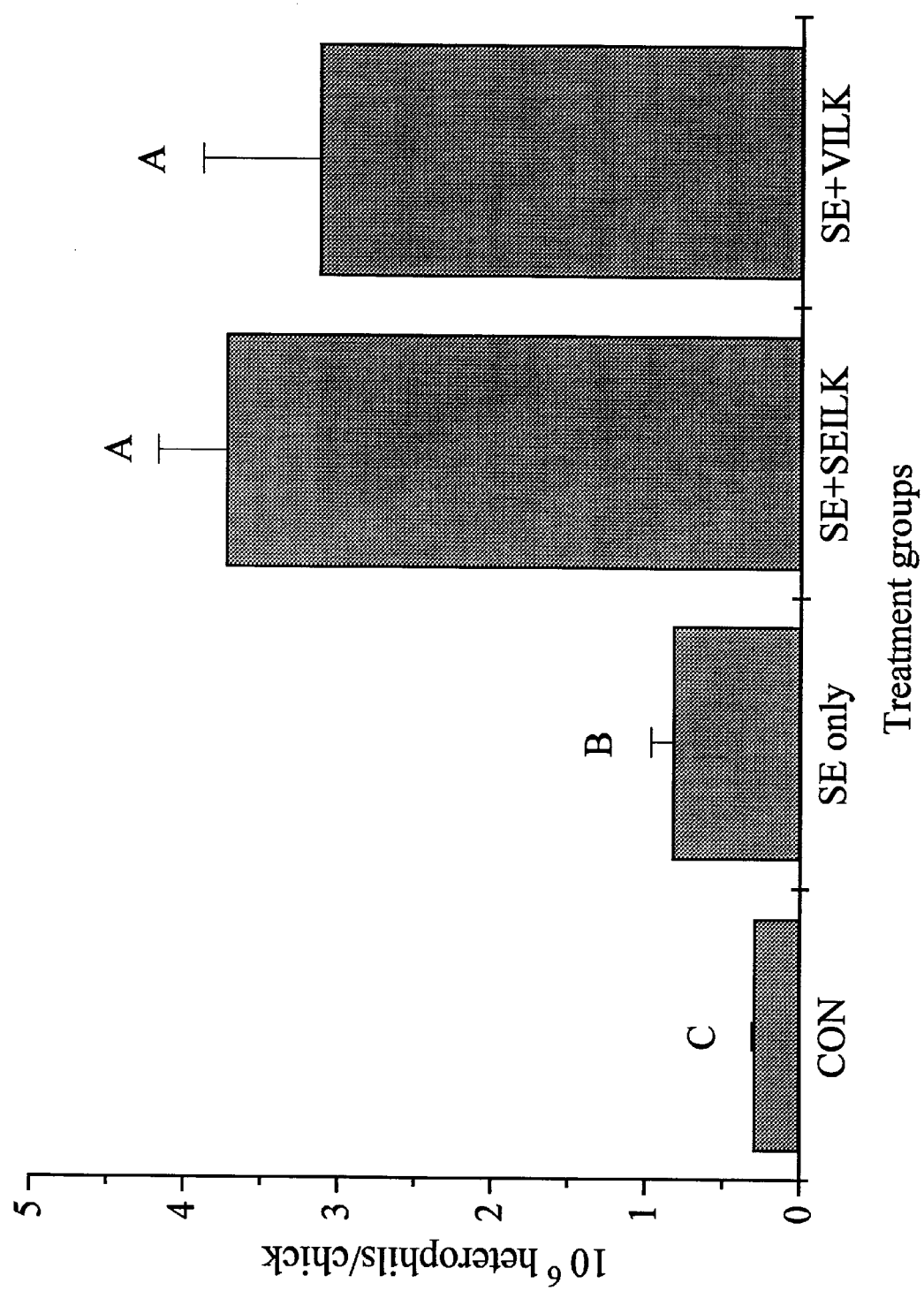
FIG. 4. Comparison of the effects of i.p. injection of SEILK versus VILK on differential peripheral blood heterophil counts.

The mean values of the number of heterophils circulation 4 hr after lymphokine injection and oral SE challenge are presented in FIG. 4. The heterophils from PBS injected control birds serve as a baseline count. Oral challenge of SE alone induced a significant increase in circulating heterophils (p<0.05); however, SEILK or VILK pretreatment induced an even higher heterophilic response (p<0.001). Comparison of the results obtained by SEILK or VILK pretreatment did not differ significantly.

Discussion

For a brief period after transformation, the T cell lines were 55% CD4+ and 30% CD8+. However, within 2 months, the T cell markers had completely disappeared from the cell surface of the transformed lines. Despite the loss of markers, our cell lines have continued to grow without the addition of cytokines and have continued to produce the immune lymphokines, retaining their protective capabilities for up to 10 months that they have been in culture. Morphologically, the cells still exhibit the characteristics of lymphocytes.

Cloning of our line has not been attempted due to the rapid loss of cell surface markers. Without markers, there is no way of distinguishing which type of cell line is responsible for the production of the protective lymphokines or if both CD4+ and CD8+ cells are needed for interaction for the production of the final product. However, the cell line does appear to be totally lymphocytic upon continued culture (>10 months). The fibroblastic, adherent cell line that was present in the first few months of culture was eventually lost due to continued transfer of the cell line.

Thus far, VILK has produced similar results to SEILK in all experimental trials. The administration of both SEILK and VILK in conjunction with live SE resulted in significant increases in 1) heterophils in circulation as seen by peripheral blood counts and 2) inflammatory heterophils in the peritoneum as demonstrated by peritoneal lavage studies. In association with increased heterophil numbers, both SEILK and VILK conferred similar degrees of resistance in the protection experiments of this study. In summary, VILK from virally transformed SE hyperimmunized chicken spleen cells enhances host defenses against organ invasion by SE by inducing the production and release of heterophils from the bone marrow into the blood within 4 hr postinjection. The lymphokine activated heterophils are then directed to the site of infection upon SE invasion of the intestine. The proinflammatory consequences of VILK administration mirror those produced by SEILK and can thus be considered a similar product.

EXAMPLE 2

The assay for the enumeration of peritoneal lavage heterophils was repeated with the treatment groups shown in Table 1 using the same procedure as described in Example 1. As indicated, the treatment groups included VILK from both cell lines ConA-Cl and ConA-BI (referred to in the Table as ConA-Cl and ConA-Bl). The VILK from both of the transformed cell lines performed as well as or greater than the original SEILK product in conjunction with SE injection.

It is understood that the foregoing detailed description is given merely by way of illustration and that modifications and variations may be made therein without departing from the spirit and scope of the invention.

TABLE 1

Peritoneal Lavage Assay comparing Heterohil numbers induced by SILK vs. VILK

| treatment | $10^6$ Heterophils/bird | | |
| --- | --- | --- | --- |
|  | expt1 | expt2 | expt3 |
| control | .01 | .03 | .004 |
| SE only | 1.23 | .56 | 68 |
| SILK only | .63 | 38 | 38 |
| SE + SILK | 2.64 | 2.48 | 1.02 |
| SE + ConA-Cl | 4.40 | 3.05 | .98 |
| SE + ConA-B1 | 4.28 | 2.78 | .98 |

We claim:

1. A method for producing an immortal cell line secreting an immune lymphokine comprising:

(a) providing T cells recovered from a fowl which has been immunized in vivo with an immunogen of a microorganism pathogenic to said fowl, said immunogen being effective to activate T cells in said fowl;

(b) exposing said T cells to a mitogen effective for secondary stimulation of said T cells;

(c) contacting the stimulated T cells from (b) with a virus effective to transforming said T cells.

2. The method as described in claim 1 wherein said fowl is selected from the group consisting of turkeys, ducks, quail, geese, pheasant, and chickens.

3. The method as described in claim 1 wherein said immunogen is selected from the group consisting of viral, bacterial, and protozoal immunogens.

4. The method as described in claim 1 wherein said immunogen comprises a Salmonella species.

5. The method as described in claim 1 wherein said mitogen is selected from the group consisting of Concanavalin A, phytohemagglutinin, and phorbol myristate acetate.

6. The method as described in claim 1 wherein said virus for transforming said T cells is an avian reticuloendotheliosis virus.

7. The method as described in claim 1 further comprising:

(d) screening the transformed T-cells from (c) for production of immune lymphokines.

8. The method as described in claim 1 wherein the stimulated T-cells from (b) are contacted with said virus in (c) in the presence of a mitogen.

9. The method as described in claim 1 wherein said T cells are splenic T cells.

10. An immortal cell line produced by the process of claim 1.

11. The immortal cell line of claim 10 wherein said cell line remains stable during cultivation in a culture medium in the absence of exogenous interleukin.

12. A method of producing an immune lymphokine comprising:
   (a) culturing the cell line of claim 10 in a culture medium containing a mitogen and under conditions effective to promote growth;
   (b) recovering immune lymphokines from said culture medium.

13. An immortal cell line produced from avian T lymphocytes and which secretes an immune lymphokine effective for protecting fowl against infection by pathogenic microorganisms.

* * * * *